United States Patent [19]
Kahn et al.

[11] Patent Number: 5,680,868
[45] Date of Patent: Oct. 28, 1997

[54] METHOD AND APPARATUS FOR DETECTING BLOOD PRESSURE BY BLOOD PRESSURE SOUNDS IN THE PRESENCE OF SIGNIFICANT NOISE

[75] Inventors: Alan R. Kahn, Minneapolis, Minn.; Dennis E. Bahr, Middleton, Wis.; Kurt W. Allen, Minneapolis, Minn.

[73] Assignee: BpSure, L.L.C., Middleton, Wis.

[21] Appl. No.: 665,286

[22] Filed: Jun. 17, 1996

[51] Int. Cl.$^6$ .................................................. A61B 5/00
[52] U.S. Cl. .......................... 128/680; 128/681; 128/682
[58] Field of Search ............................ 128/677, 680-3, 128/687

[56]  References Cited

U.S. PATENT DOCUMENTS

| | | |
|---|---|---|
| 3,773,033 | 11/1973 | Rodbard et al. . |
| 4,005,701 | 2/1977 | Aisenberg et al. . |
| 4,245,648 | 1/1981 | Trimmer et al. ..................... 128/686 |
| 4,313,445 | 2/1982 | Georgi . |
| 4,396,018 | 8/1983 | Sibley . |
| 4,408,614 | 10/1983 | Weaver et al. . |
| 4,592,365 | 6/1986 | Georgi . |
| 4,649,929 | 3/1987 | Weaver et al. . |
| 4,819,654 | 4/1989 | Weaver et al. . |
| 4,840,181 | 6/1989 | Yamaguchi ........................... 128/681 |
| 4,938,227 | 7/1990 | Niwa et al. . |
| 5,031,630 | 7/1991 | Hirano et al. . |
| 5,135,003 | 8/1992 | Souma . |
| 5,337,750 | 8/1994 | Walloch . |
| 5,392,781 | 2/1995 | Phillipps et al. . |

OTHER PUBLICATIONS

Kim–Gau Ng & Carolyn F. Small, "Survey of Automated Noninvasive Blood Pressure Monitors", J. Clinical Engineering, vol. 19, No. 6, pp. 452–475, Nov./Dec. 1994.

*Primary Examiner*—Robert Nasser
*Attorney, Agent, or Firm*—Foley & Lardner

[57]  ABSTRACT

A method and apparatus is provided for detecting blood pressure sounds produced by the opening snap of an artery in a patient in the presence of significant noise using the phase information contained in two microphone signals. The two microphones are placed on a patient along the axis of an artery with their centers separated by a distance such that blood pressure sounds picked up by the microphones will be out of phase. Pressure is applied to the artery such that the artery opens and closes during each heart cycle, the opening snap of the artery producing blood pressure sounds. The two microphone signals are filtered, preferably using band pass filters having pass bands corresponding to the frequency of the blood pressure sounds. The filtered microphone signals are sampled and multiplied together or convolved in the frequency domain to generate a microphone signal product. If the microphone signal product is negative, the detection of a valid blood pressure signal for that sampling time is indicated. In an alternative embodiment, the slope of the two microphone signals at the sample time is also determined. A valid blood pressure signal is indicated when the microphone signal product is negative and either the two microphone signal slopes have inverse signs or are both less than a selected slope threshold. A selected number of consecutive valid blood pressure signal detections indicates the detection of a blood pressure sound. The detection of blood pressure sounds at a range of cuff pressures is used to determine the systolic and diastolic blood pressure levels of the patient.

45 Claims, 6 Drawing Sheets

METHOD AND APPARATUS FOR DETECTING BLOOD PRESSURE BY BLOOD PRESSURE SOUNDS IN THE PRESENCE OF SIGNIFICANT NOISE

FIELD OF THE INVENTION

This invention pertains generally to the field of blood pressure monitoring methods and devices, and more particularly to blood pressure monitoring devices and methods employing one or more microphones for detecting the onset and disappearance of blood pressure sounds as pressure is applied to the brachial artery of a patient.

BACKGROUND OF THE INVENTION

A common method for measuring the blood pressure of a patient employs an inflatable cuff (sometimes referred to as a Riva-Rocci cuff) wrapped around the upper arm of the patient whose blood pressure is to be determined. As the cuff is inflated, the cuff pressure, and the pressure applied to the arm of the patient, increases. If the pressure applied to the arm is increased beyond the highest blood pressure level in a brachial artery located in the arm beneath the cuff, the artery will be forced closed.

The blood pressure in the brachial artery is not constant, but varies with time in relation to the beating of the heart. Following a contraction of the heart to pump blood through the circulatory system, the blood pressure increases to a maximum level. This level is known as the systolic blood pressure level. The minimum blood pressure level between heart beats is known as the diastolic blood pressure level.

As the pressure in the inflatable cuff is reduced from a high level above the systolic blood pressure level, where the brachial artery is forced permanently closed, to below the systolic blood pressure level, the brachial artery beneath the cuff will begin to open and close with each heart beat as the blood pressure level first exceeds the cuff pressure and then falls below the cuff pressure. The arterial wall acts in a non-linear fashion with respect to the blood pressure level. Thus, as the blood pressure exceeds the cuff pressure, the artery will literally "snap" open, producing a low frequency blood pressure sound. This blood pressure sound may be detected using a microphone placed under the cuff against the patient's arm. The turbulent flow of blood through the artery following the opening snap also produces sounds, known as Korotkoff sounds, that may be detected using a stethoscope or microphone placed near the down-stream end of the cuff on the patient's arm. The highest cuff pressure at which Korotkoff sounds or blood pressure sounds are detectable thus corresponds to the systolic blood pressure level of the patient.

As the cuff pressure is reduced further, the cuff pressure will be brought below the diastolic blood pressure level. At this pressure level, the brachial artery beneath the cuff remains open throughout the heart beat cycle. Blood pressure sounds, caused by the opening of the artery, and Korotkoff sounds, will, therefore, not be produced. The lowest cuff pressure at which blood pressure sounds or Korotkoff sounds can be detected thus corresponds to the diastolic blood pressure level of the patient. The determination of blood pressure levels in this manner, based on the detection of the onset and disappearance of Korotkoff sounds or blood pressure sounds as varying pressures are applied to an artery, is known as an auscultatory method of blood pressure determination.

In manual auscultatory blood pressure measurement methods, a stethoscope is used to detect the onset and disappearance of Korotkoff sounds. Thus, the blood pressure measurement made will be highly dependent on the skill and hearing ability of the person taking the measurement. To overcome this dependence on human skill and judgement, and to automate the process of determining a patient's blood pressure, automatic blood pressure monitoring systems based on the auscultatory method of blood pressure determination have been developed. These automatic systems employ one or more microphones placed in or under an automatically inflatable and deflatable cuff to detect blood pressure sounds. However, movement of the patient under examination, such as during exercise, and other activity around the patient will cause noise to be picked up by the blood pressure monitor microphones along with the blood pressure sounds. The automatic blood pressure monitoring system must, therefore, be able to separate the noise from the blood pressure sounds in order to accurately determine the patient's blood pressure levels. This has been achieved, for example, by filtering the microphone signal using a band pass filter whose pass band corresponds to the known frequency range of blood pressure sounds. This eliminates much of the noise from the microphone signal.

Some automatic blood pressure monitoring systems employ two microphones for detecting blood pressure sounds. For example, two microphones may be placed under the inflatable cuff separated by a distance such that a low frequency blood pressure sound will reach the first microphone 180° out of phase from the second microphone. Noise signals will tend to reach each microphone essentially simultaneously, and in phase. Therefore, subtracting the two microphone signals from each other will tend to enhance the useful data and diminish unwanted noise. The two microphone signals can be added and subtracted from each other to create signal and noise detection thresholds. Microphone signals are considered to be valid blood pressure sound detections if they meet the detection thresholds.

Another method that makes use of two microphones relies on using a first microphone placed on the arm of the patient upstream from a second microphone to provide a time gate for the second microphone. Once again, this method relies on the fact that blood pressure sounds will propagate down the arm of the patient from the first microphone to the second microphone, whereas a noise signal will likely be picked up by both microphones simultaneously. When a sound signal exceeding a certain threshold is picked up by the first microphone, a time gate is opened which causes the downstream microphone to "listen" during a time interval a few milliseconds later, corresponding to the estimated propagation time of a blood pressure sound between the two microphones. If a sound signal is picked up by the second microphone during the gate period, the signal may be considered to be a valid blood pressure sound detection. A similar gating scheme may be used for blood pressure monitors employing a single microphone. Since the time delay between the contraction of the heart and the appearance of a blood pressure sound at the microphone placed on the arm of a patient can be estimated, a signal from an ECG heart monitor may be used to generate a delayed gate for the blood pressure monitor microphone. A sound signal picked up by the microphone during the gate period may be considered a valid blood pressure sound detection.

Each of the prior art automatic blood pressure monitoring methods described tends to help obtain useful data in moderately noisy environments. However, these systems are less effective when confronted with significant noise levels. Significant noise levels can be the result of significant body motion and vibrations caused, for example, by shivering or exercise of the patient. Significant noise levels can also be caused by ambient vibration and noise in highly noisy environments, such as in ambulances or helicopters in which a patient is being transported. In the presence of significant noise, the useful signals picked up by the microphones are often much smaller than the noise signals. This limits the effectiveness of using signal and noise thresholds to detect blood pressure sounds, as this technique relies on amplitude as well as phase characteristics of the blood pressure sound signal for making detections. While the technique of using one microphone to open a listening gate for another microphone will assist in detecting the useful signal, it will not perform properly in highly noisy environments where noise is likely to occur during the listening interval of the downstream microphone.

SUMMARY OF THE INVENTION

The present invention provides a method and apparatus for monitoring the blood pressure of a patient by detecting low frequency blood pressure sounds, produced by the opening of an artery, in the presence of significant noise levels. The present invention employs two microphones placed over the brachial artery of a patient to detect the onset and disappearance of blood pressure sounds in the artery as the pressure on the artery is varied. The microphones are placed on the patient separated by a distance such that a true blood pressure sound will preferably be picked up at the second microphone approximately 180° out of phase with respect to the blood pressure sound picked up by the first microphone. The shift in phase between the signals from the two microphones is used to indicate the detection of a blood pressure sound in the presence of significant noise levels. Since no time gate is employed, it does not matter which of the two microphones is placed upstream of the other. The manner in which the phase shift information of the two microphones signals is analyzed enables accurate blood pressure measurements to be made during the extremes of noise interference encountered during patient movement, shivering, or exercise, or caused by ambient vibrations encountered in highly noisy environments. The present invention identifies the useful blood pressure sound signals from phase information in a manner in which signal and noise amplitude is not a factor. Thus, the present invention does not depend on the calculation of signal or noise thresholds. The present invention does not require that all of the noise be filtered out. Thus, the present invention makes possible the detection of useful blood pressure signals among much larger noise signals.

The method and apparatus of the present invention for detecting blood pressure by sounds in the presence of noise may be used in an automatic blood pressure monitoring system employing an inflatable cuff that is wrapped around the arm of a patient whose blood pressure is to be monitored. The two microphones are placed under the cuff against the patient's arm. The microphones are preferably fixed within the cuff near the down stream end of the cuff and are placed along the axis of a brachial artery. The centers of the two microphones are separated by a distance such that a blood pressure sound signal picked up by one of the microphones will be picked up out of phase (preferably approximately 180° out of phase) at the second microphone. The pressure in the inflatable cuff may be controlled by a pressure controller, including a pump and one or more valves, that is capable of inflating the cuff to a pressure level above the maximum probable systolic blood pressure level, and of gradually lowering the pressure in the cuff from this high pressure level to a pressure level below the diastolic blood pressure level at which blood pressure sounds are no longer detected. A pressure transducer in the cuff or pressure controller is employed to determine the amount of pressure in the cuff. The pressure transducer signal is preferably converted to a digital signal for storage and use by a digital microprocessor based system controller that is used to control the pressure controller and to determine the patient's blood pressure levels based on the pressure transducer output and the blood pressure sounds detected by the microphones.

In accordance with the present invention, the indication of the detection of a blood pressure sound is based upon the phase shift information in the signals from the two microphones. Low frequency blood pressure sounds, produced by the opening "snap" of the brachial artery each heart cycle, appear approximately 180° out of phase at the two microphones. Noise signals, arising from various sources of interference, travel at approximately the speed of sound and arrive simultaneously and substantially in phase at the two microphones, even though they may have different amplitudes at each microphone location. In accordance with the present invention, the signals from the two microphones are first filtered to select the frequencies or other characteristics of the microphone signals corresponding to the blood pressure sounds produced by the opening of the brachial artery. This may preferably be accomplished using a band pass filter. The desired bandwidth is in the range of approximately 30 Hz to 80 Hz. At a corresponding center frequency for the blood pressure sounds of 50 Hz, the centers of the two microphones are placed approximately 2.5 centimeters apart to provide the desired 180° phase shift between the blood pressure sound signals picked up at the two microphones.

The filtered microphone signals are preferably converted to digital signals that are provided to a digital microprocessor that extracts the phase shift information from the two signals to indicate the detection of blood pressure sounds in the presence of significant noise. To extract the phase shift information from the two microphone signals, the two signals are sampled at a relatively high rate (500 Hz–2000 Hz). At each sample time, a value corresponding to the state (amplitude and sign) of each filtered microphone signal is determined, the two signals are multiplied together, and a valid blood pressure signal is indicated as detected if the product of the two signals yields a negative value. A negative value indicates that the two signals are out of phase at that sample time, which is, in turn, an indication that a blood pressure sound is being detected. The microphone signal product value may be generated directly in a conventional manner, in the time domain, or the two microphone signals may be converted to the frequency domain using a fast Fourier or sliding Fourier transform, and then convolved to produce the microphone signal product value.

In another embodiment of the present invention, for extracting phase shift information indicative of blood pressure sounds from the microphone signals, and for ignoring amplitude information that may be caused by noise, a combined calculation using the slopes of the two microphone signals may be used. A value for the slope of each of the two microphone signals may be calculated using data from adjacent sample points occurring before and/or after the point being analyzed. This slope information, along with the product information described previously, is used in a composite calculation to indicate the detection of a valid blood pressure signal. If the product of the two microphone signals yields a negative value, and either the slopes of the two microphone signals have inverse signs or the slopes of both microphone signals are less than a certain slope threshold, a valid blood pressure signal is indicated as detected for that sample time.

If consecutive valid blood pressure signals are indicated as being detected for more than a selected period of time, e.g., 2.5 ms, the detection of a blood pressure sound is indicated. After a blood pressure sound has been detected, further sampling data is preferably ignored for a selected pause period, to prevent multiple blood pressure sounds from being detected following a single heart beat.

The blood pressure sound detection method of the present invention allows blood pressure sounds produced by the opening of an artery to be detected in the presence of significant noise levels. The phase detection method of the present invention is only slightly affected by interference entering the microphones. Since phase information alone is used, rather than both phase and amplitude information, signal and noise sensing thresholds are not used, and need not be calculated. This is an advantage over prior art two-microphone methods that require the calculation and updating of signal and noise threshold levels.

The detection of a true blood pressure sound indicates the occurrence of the opening of the brachial artery. By identifying the detection of blood pressure sounds in this manner, the systolic and diastolic blood pressure levels of a patient can be accurately determined in the presence of significant noise levels using auscultatory blood pressure determination methods. Thus, for example, the cuff pressure may be inflated to a pressure level above the maximum probable systolic blood pressure level of the patient. The pressure level in the cuff is then gradually reduced. Blood pressure sounds are detected in accordance with the present invention. Each time a blood pressure sound is indicated as being detected, the corresponding cuff pressure is recorded. The maximum cuff pressure at which blood pressure sounds are first detected corresponds to the systolic blood pressure level of the patient. The cuff pressure at which the detection of blood pressure sounds disappears corresponds to the diastolic blood pressure level of the patient. The systolic and diastolic blood pressure levels may be determined in this manner by the blood pressure monitor microprocessor, and displayed to an operator on a user display.

The method of the present invention for detecting blood pressure sounds in the presence of significant noise may be used in any blood pressure monitoring system or method requiring the accurate detection of blood pressure sounds. For example, blood pressure sounds may be accurately detected during cuff inflation, as well as during cuff deflation. Thus, accurate systolic and diastolic blood pressure levels may be determined during the process of inflating the cuff from below the minimum probable diastolic blood pressure level to above the systolic blood pressure level at which blood pressure sounds are no longer detectable.

Though preferably implemented using a digital microprocessor, the detection of blood pressure sounds in the presence of significant noise in accordance with the present invention may be accomplished using analog circuitry or a combination of analog and digital components. Thus, for example, the multiplication of the filtered microphone signals may be accomplished in a digital microprocessor or by using an analog multiplier. Similarly, the slopes of the two microphone signals may be determined using analog or digital components.

A method and apparatus in accordance with the present invention for detecting blood pressure sounds in the presence of significant noise, and for determining accurate systolic and diastolic blood pressure levels therefrom, has several advantages over previous blood pressure monitoring methods and devices. The present invention enables accurate detection of blood pressure sounds and measurement of blood pressure levels in the presence of significant noise caused by patient movement, shivering, and exercise, and by ambient vibration and noise. The present invention also enables the accurate measurement of blood pressure during low flow states, such as cardiogenic shock, wherein the amplitude of blood pressure sounds is very small and can, therefore, become dominated by even moderate noise levels. In such low flow states, the opening snap of the artery may still be detected even though the blood flow turbulence level is too small to produce Korotkoff sounds. Since the present invention relies on phase, rather than amplitude, information to detect blood pressure sounds, a blood pressure monitoring method or apparatus in accordance with the present invention may be applied to a wide variety of patient types without the necessity for calculating signal and noise threshold values and for making signal and noise threshold adjustments for each patient.

Further objects, features, and advantages of the invention will be apparent from the following detailed description of the invention taken in conjunction with the accompanying drawings.

DETAILED DESCRIPTION OF THE INVENTION

Figure 1:
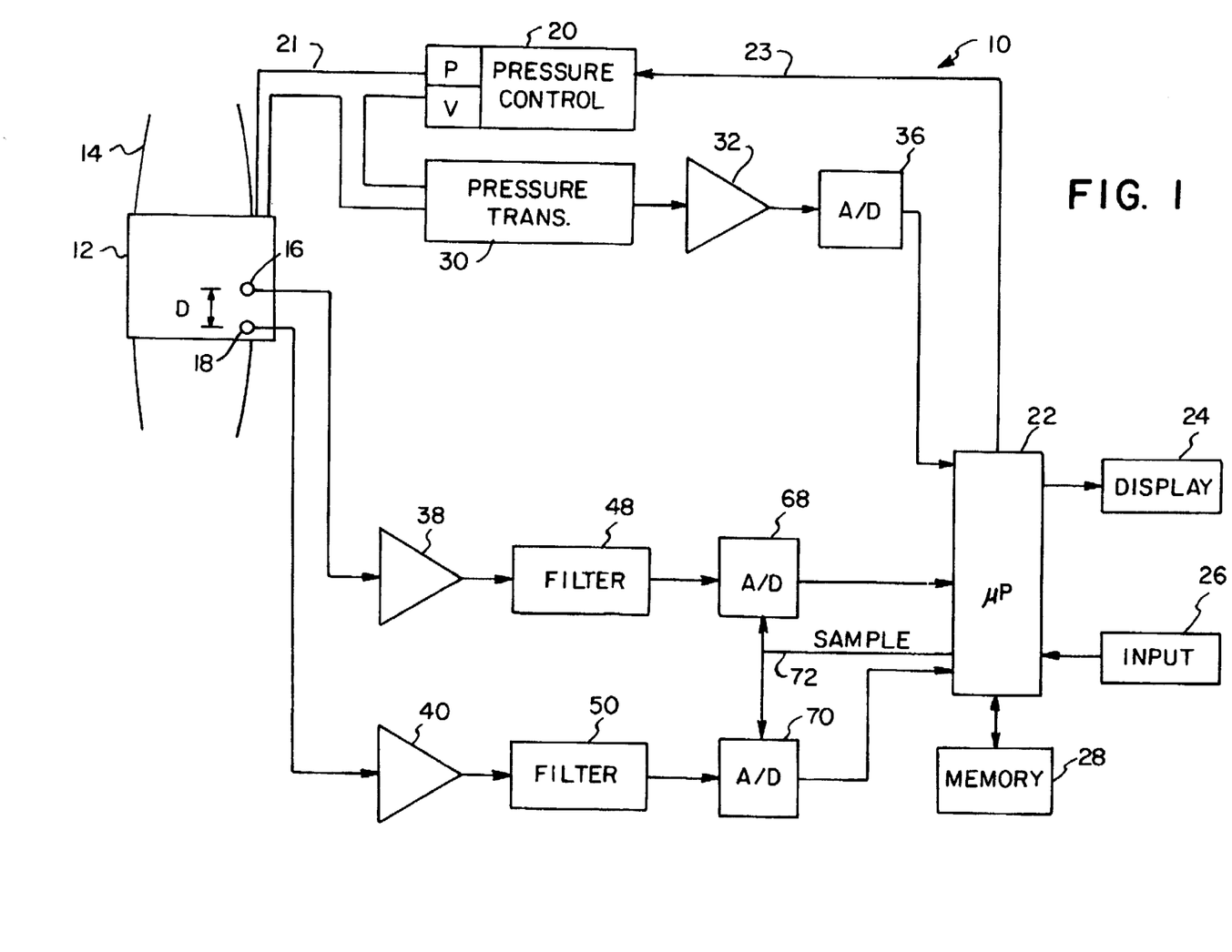
FIG. 1 is a schematic block diagram of a blood pressure monitoring system in accordance with the present invention.

A schematic block diagram of an automatic blood pressure monitoring system 10 employing the present invention is presented in FIG. 1. It should be understood that the present invention may be employed in other automatic blood pressure monitoring system topologies as well. The blood pressure monitoring system 10 preferably includes an inflatable cuff 12 that is adapted to be wrapped around the arm 14 or other appendage of a patient whose blood pressure is to be monitored. By inflating the cuff 12, pressure is applied to a brachial artery in the arm 14 of the patient, forcing the artery closed during at least part of the patient's heart beat cycle. When the pressure in the cuff 12 is increased above the systolic blood pressure of the patient, the brachial artery in the arm 14 will become closed off entirely. The arterial wall acts in a non-linear fashion with respect to the blood pressure level. Thus, as the pressure in the cuff 14 is released to below the systolic blood pressure level, but above the diastolic blood pressure level, the brachial artery will literally "snap" open following each beat of the patient's heart. This produces low frequency blood pressure sounds that are picked up by microphones 16 and 18 placed on the arm 14 of the patient beneath the cuff 12. Korotkoff sounds, produced primarily by the turbulent flow of blood through the artery following the opening of the artery, may also be picked up by the microphones 16 and 18. It should be noted that the present invention is focused on the detection of the low frequency sounds produced by the opening snap of the artery, rather than blood flow sounds. It is in this sense that the term "blood pressure sounds" is used throughout this description.

The microphones 16 and 18, which are preferably fixed in the cuff 12, are placed on the arm 14 of the patient near the down-stream end of the cuff 12, and along the axis of the brachial artery. The centers of the microphones are separated by a distance D such that blood pressure sounds are picked up by each microphone approximately 180° out of phase. When the pressure in the cuff 12 is reduced below the diastolic blood pressure level, the brachial artery will remain opened between heart beats, and the low frequency blood pressure sounds produced by the opening of the artery will disappear.

Although the cuff 12 may be manually inflated and deflated, the pressure in the cuff 12 is preferably controlled automatically by a pressure controller 20. The pressure controller 20 is connected to the cuff 12 by a tube 21, and may be of a conventional design used in commercially available automatic blood pressure monitoring systems. The pressure controller 20 may, for example, include a conventional pump P for inflating the cuff 12, and one or more conventional valves V for releasing pressure from the cuff 12. The pressure controller 20 is preferably capable of inflating the cuff 12 to a cuff pressure exceeding the systolic blood pressure level of a patient, and of slowly reducing the cuff pressure from this high level to a low pressure level below the diastolic blood pressure level of the patient, either continuously or in step-wise fashion.

The pressure controller 20 is preferably operated to inflate and deflate the cuff 12 under control of a system digital microprocessor 22 that provides control signals to the pressure controller on a line 23. As described in more detail below, the system microprocessor 22 may be used to control the pressure controller 20 to implement a blood pressure monitoring cycle, to derive phase information from signals provided by the microphones 16 and 18 to detect blood pressure sounds, and to determine the patient's systolic and diastolic blood pressure levels based on the detected blood pressure sounds and corresponding cuff pressure levels. A user display 24, such as a monitor, printer, LED display, or any other conventional display system, is preferably connected to the microprocessor 22 for the display of the patient's blood pressure levels and other information required by a user. The microprocessor 22 preferably also is connected to a user input 26. The user input 26 may include a keyboard, switch, push button, or other input mechanism, whereby, for example, a blood pressure monitoring cycle may be initiated, and/or operator or patient information may be entered into the system. The microprocessor 22 also preferably includes an associated memory 28, e.g., RAM, which may be implemented as a separate memory unit 28, as shown, or as an integral part of the microprocessor 22. The memory 28 is used in a conventional manner by the microprocessor 22 for the storage of, for example, valid blood pressure signal information from the microphones 16 and 18, corresponding cuff pressures, and operator or patient information input by the user through the user input 26.

Figure 2:
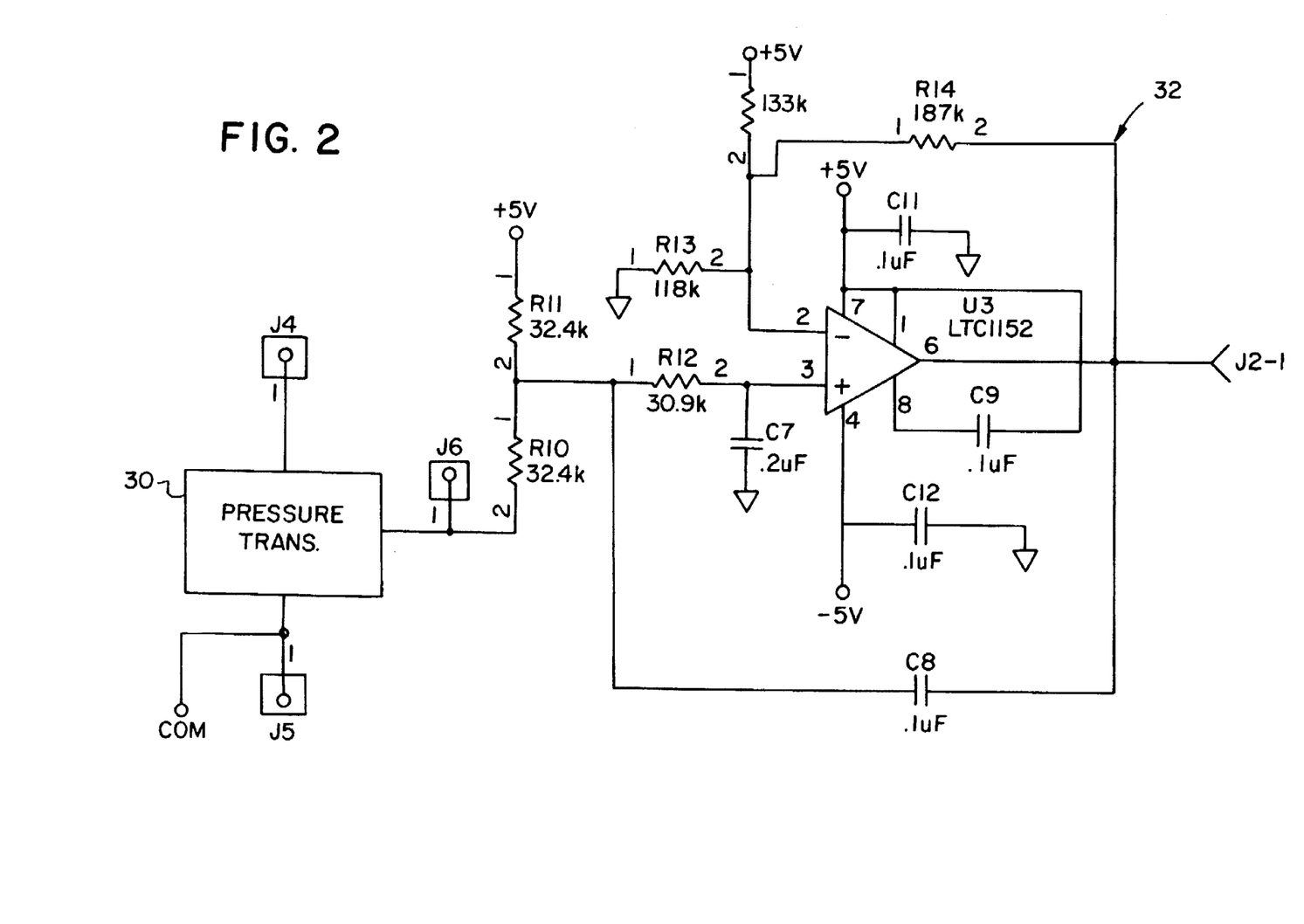
FIG. 2 is a schematic circuit diagram of a pressure transducer and amplifier for use in a blood pressure monitoring system in accordance with the present invention.

The pressure in the cuff 12 at any point in time may preferably be determined using a pressure transducer 30 which may be mounted in the cuff 12, in the tube 21 connecting the cuff 12 to the pressure controller 20, or in the pressure controller 20 itself. The pressure transducer output may be filtered to reduce unwanted noise, and is applied to an amplifier 32. A conventional amplifier circuit may be used to amplify the pressure transducer signal. An exemplary amplifier circuit 32 that may be used in the blood pressure monitoring system 10 is illustrated in FIG. 2. The amplified analog pressure signal is preferably converted to a digital signal by an analog-to-digital converter 36. Note that the analog-to-digital converter 36 may be implemented as a separate circuit component, as illustrated in FIG. 1, or may be an integral part of the microprocessor 22. The digital pressure signal from the analog-to-digital converter 36 is provided to the microprocessor 22 which may store the pressure signal value in memory 28 for later use in determining the patient's systolic and diastolic blood pressure levels. Using the pressure signal received from the analog-to-digital converter 36, the microprocessor 22 is also able to provide control signals to the pressure controller 20 on the line 23 to cause the pressure controller 20 to increase or decrease the pressure in the cuff 12 to a desired level.

Figure 3:
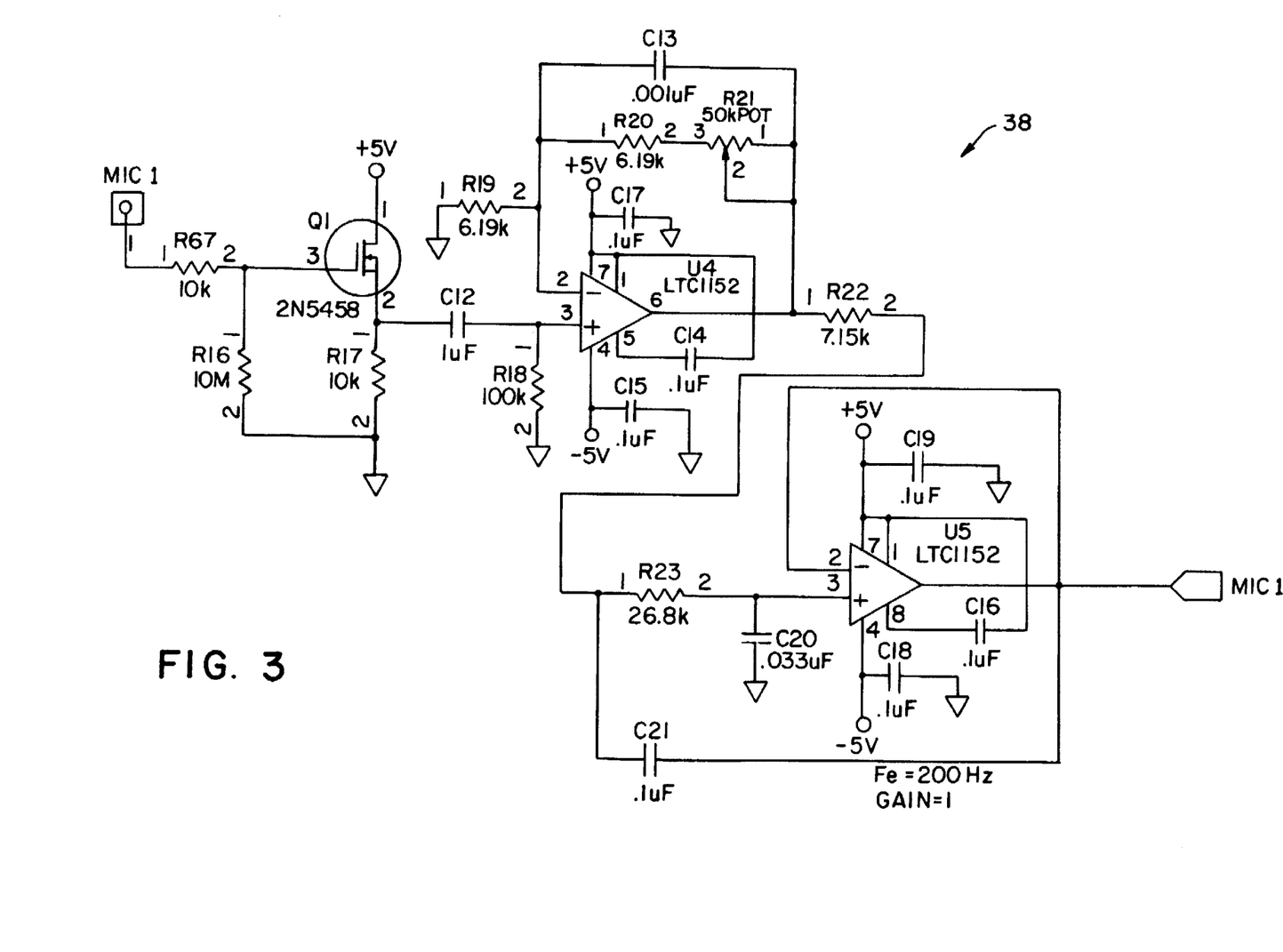
FIG. 3 is a schematic circuit diagram of a microphone signal amplifier for use in a blood pressure monitoring system in accordance with the present invention.

The microphones 16 and 18 may be implemented in a conventional manner using commercially available microphones, sound pick-ups, transducers, etc. Sound signals picked up by the microphones 16 and 18 are amplified by microphone amplifiers 38 and 40, respectively. Conventional microphone amplifier circuits may be used to implement the microphone amplifiers 38 and 40. A preferred microphone amplifier circuit 38 is illustrated in FIG. 3. (Note that the other microphone amplifier 40 may be implemented using an identical circuit.) For the amplifier circuit embodiment of FIG. 3, the output of the amplifier 38 is a −5 volt to +5 volt analog signal corresponding to the sound signal picked up by the microphone 16. The output of the microphone amplifier 40 is a similar analog signal.

The sound signal of interest to be detected by the microphones 16 and 18 is the low frequency blood pressure sound produced by the snapping open of the brachial artery. This sound has a characteristic frequency component in a known frequency range. Sound signal components picked up by the microphones 16 and 18 that are outside of this range are, therefore, probably noise. The detected and amplified microphone signals are thus preferably filtered by band pass filters 48 and 50 to select the frequencies corresponded to the signals of interest and to reject other frequencies which are characteristic only of noise. The desired bandwidth for blood pressure sounds is in the range of approximately 30 Hz to 80 Hz, with a center frequency of about 50 Hz. Other bandwidth ranges besides this one may also be used in accordance with the present invention; however, the low frequency blood pressure sounds produced by the snapping open of the brachial artery are generally characterized by frequencies limited to the 10 Hz–100 Hz frequency range.

Figure 4:
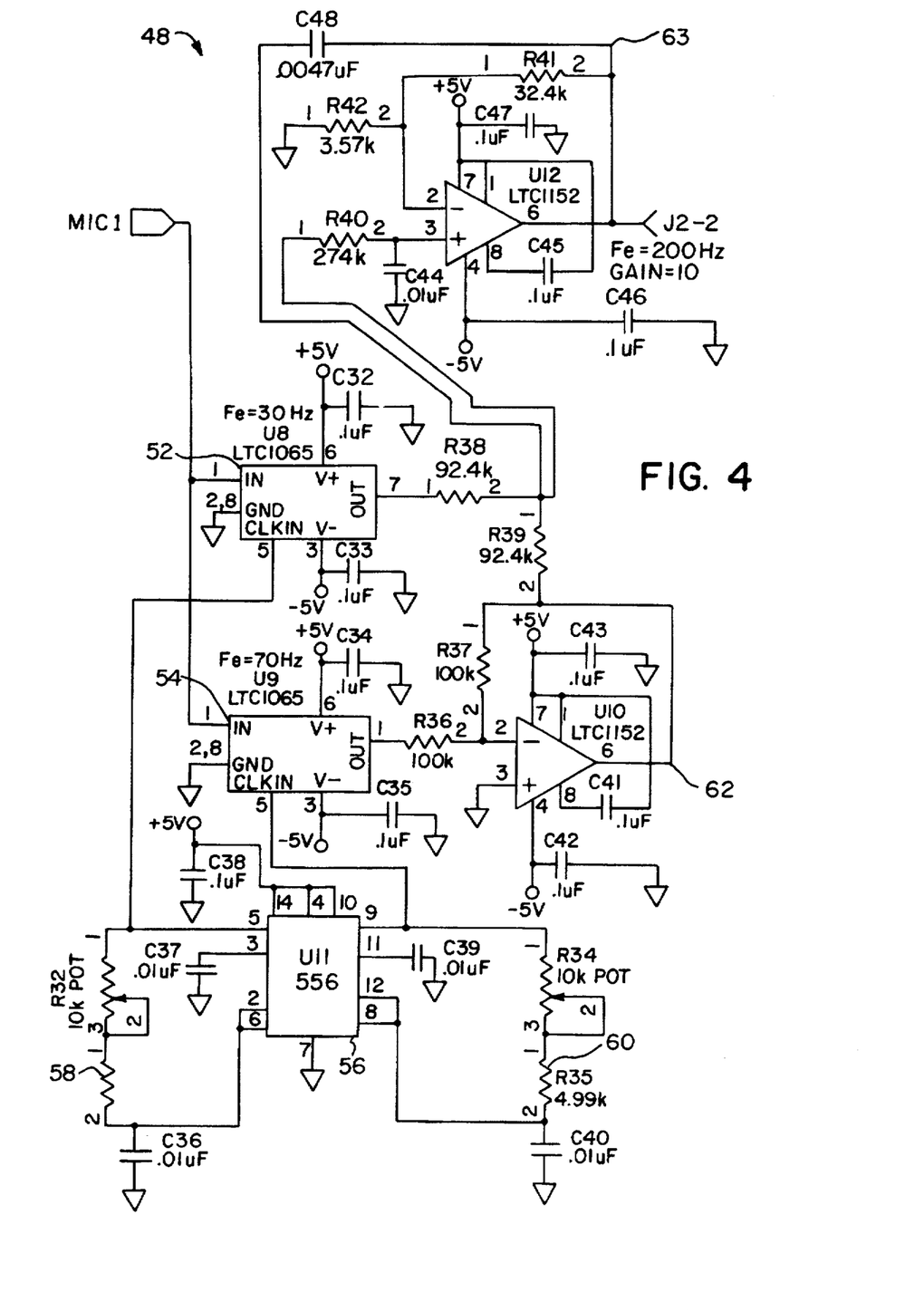
FIG. 4 is a schematic circuit diagram of a band pass filter for filtering microphone signals in a blood pressure monitoring system in accordance with the present invention.

The band pass filters 48 and 50 may be implemented in a conventional manner, using known band pass filter circuit topologies. An example of a band pass filter circuit 48 for filtering the signal from the first microphone 16 is illustrated in FIG. 4. (The band pass filter 50 for the signal from the second microphone 18 may be similarly implemented). The exemplary band pass filter topology includes two integrated circuit low pass filters 52 and 54. The incoming amplified microphone signal is applied to each of the low pass filters 52 and 54. A separate clocking signal is applied to each filter 52 and 54 from an integrated circuit oscillator 56. The frequency of the first clocking signal, e.g., 3000 Hz, that is applied to the first low pass filter 52, is set by an RC circuit 58 connected to the integrated circuit oscillator 56. The value of the resistance in the RC circuit 58 may be adjusted to determine the clocking frequency applied to the first low pass filter 52. A higher frequency clocking signal, e.g., 8000 Hz, is provided by the integrated circuit oscillator 56 to the other low pass filter 54. The frequency of this clocking signal is determined by the RC circuit 60 connected to the integrated circuit oscillator 56. The resistance value of the RC circuit 60 may be adjusted to determine the clocking frequency. The clocking frequencies applied to the low pass filters 52 and 54 set the pass bands of the filters. In this case, the filter cut off frequencies are the clocking frequencies divided by 100. Each integrated circuit low pass filter 52 and 54 passes the portion of the incoming amplified microphone signal whose frequency component does not exceed the pass band of the respective filter. Thus, in this exemplary case, the output of the first low pass filter 52 includes the amplified microphone signal frequency components less than 30 Hz, and the output of the second low pass filter 54 includes the amplified microphone signal frequency components that are less than 80 Hz. The output of the second, higher frequency, low pass filter 54 is inverted by inverting amplifier circuit 62. The output of the inverter circuit 62 is then added to the output of the first, lower frequency, low pass filter 52 at a second amplifier circuit 63. Thus, the amplifier circuits 62 and 63 effectively subtract the output of the higher frequency low pass filter 54 from the output of the lower frequency low pass filter 52. It is apparent, therefore, that the output of the second amplifier circuit 63, which is the output of the band pass filter 48, includes only the amplified microphone signal frequency components in a pass band defined by the low pass filter frequencies, in this case, 30–80 Hz.

It should be noted that filtering of the microphone signals need not be limited to conventional band pass filtering. For example, filtering out low frequency noise from the microphone signals is more critical than filtering out high frequency components from the microphone signals. Thus, the filters 48 and 50 may also be implemented as high pass filters. In general, for purposes of the present invention, the terms "filtering" and "filter" should be understood to encompass any method or apparatus for selecting a portion of the microphone signal having characteristics of blood pressure sounds and rejecting portions of the microphone signal characteristic of noise. These characteristics may be, but need not be, frequency components of the microphone signals.

The analog outputs of the filters 48 and 50 are preferably converted to digital signals by analog-to-digital converters 68 and 70, respectively. Note that the analog-to-digital converters 68 and 70 may be implemented as separate components, as illustrated, or may be integral parts of the system microprocessor 22. The outputs of the analog-to-digital converters 68 and 70, corresponding to digitized filtered signals from microphones 16 and 18, are provided to the microprocessor 22, that employs the received digital signals to detect blood pressure sounds in the presence of significant noise in the manner to be described in more detail below.

In accordance with the present invention, blood pressure sounds produced by the snapping open of the brachial artery are detected based upon phase shift information in the signals from the two microphones 16 and 18. Since the present invention does not employ time gating, it does not matter which microphone 16 or 18 is placed upstream of the other. However, both microphones 16 and 18 are preferably placed along the axis of the brachial artery. The centers of the two microphones 16 and 18 are separated by the distance D such that a blood pressure sound will be picked up approximately 180° out of phase by each microphone. The low frequency blood pressure sound produced by the snapping open of the brachial artery represents a relatively slow pulse wave when compared with the speed of sound at which most noise signals will travel. Thus, for two microphones 16 and 18 having centers separated by a distance D, whereas the signal of interest, the blood pressure sound signal, will be out of phase for each microphone 16 and 18, a noise signal will be picked up essentially simultaneously and in phase by each microphone 16 and 18.

As discussed previously, the frequency range of interest for blood pressure sounds is approximately 30 Hz to 80 Hz, with a center frequency of about 50 Hz. At 50 Hz, the time required to complete one cycle is 20 milliseconds. To produce the maximum phase shift between the two microphone signals, therefore, the centers of the two microphones 16 and 18 should be separated by a distance D that produces a delay in the detected blood pressure sound pulse equivalent to ½ of a cycle, i.e., 10 milliseconds. It is known that the pulse wave produced by the blood pressure sound propagates down the arm 14 at approximately 2.5 meters per second. Thus, centering the microphones 16 and 18 approximately D=2.5 centimeters apart provides the desired 10 millisecond delay between the signals from each microphone 16 and 18. The microphones 16 and 18 may be fixed in the cuff 12 at this separation distance. Analysis of signals obtained during tests on human subjects reveal maximum phase shifts when these parameters are used. It should be noted that a slightly larger or smaller distance D between the centers of the two microphones 16 and 18 may be used without dramatically affecting the ability of the present invention to detect blood pressure sounds in the presence of significant noise. The separation distance D should, however, be such that blood pressure sounds picked up by the microphones 16 and 18 are at least 90° out of phase.

In accordance with the present invention, phase shift information is extracted from the two microphone signals to determine whether the signal detected at any one point in time represents a signal corresponding to a valid blood pressure sound. Such a signal is designated as a valid blood pressure signal. If a consecutive series of valid blood pressure signals are detected, the detection of a blood pressure sound is indicated. To extract phase shift information from the two microphone signals, the two amplified and filtered microphone signals are preferably sampled at a relatively high rate, e.g., 500 Hz–2000 Hz. This may be accomplished, for example, by a SAMPLE signal applied at the desired frequency to the analog-to-digital converters 68 and 70 from the microprocessor 22 on a line 72. This SAMPLE signal causes the digital signals corresponding to the filtered microphone signals to be provided to the microprocessor 22 at the desired sampling rate. Of course, the sampling may be accomplished entirely internal to the microprocessor 22, particularly where the analog-to-digital converters 68 and 70 are implemented as integral parts of the microprocessor 22.

At each sample time a value for the state (amplitude and sign) of each of the microphone signal values is selected. The two sampled microphone signals are multiplied together to generate a microphone signal product. This multiplication may be accomplished directly, in the time domain, or may be achieved by transforming the microphone signals into the frequency domain and then convolving the two transformed signals. If the product of the two signal values yields a negative value, the detection of a valid blood pressure signal is indicated. This is because a negative product indicates that the signals are out of phase, which is the expected case for blood pressure sounds picked up by the microphones 16 and 18. It is preferable that the absolute value of the product of the two microphone signals also exceed some relatively small fixed threshold before the detection of a valid blood pressure signal is indicated. This is to account for the relatively low level of system noise.

It is apparent that the foregoing calculation extracts phase shift information from the two microphone signals, which is indicative of blood pressure sounds, and entirely ignores amplitude information in the two microphone signals, which can be affected by noise. This is achieved by multiplication of the two microphone signals, rather than adding or subtracting the signals to form signal and noise thresholds in the conventional manner.

An alternative method in accordance with the present invention for indicating a valid blood pressure signal detection incorporates a second calculation using the slopes (or derivatives) of the two microphone signals. At each sample time, a value for the slope of each of the two microphone signals is calculated. This slope value may be calculated using data from adjacent sample points occurring before and/or after the point being analyzed. Thus, the slope of a microphone signal may be calculated as the rate of change of the filtered microphone signal between adjacent sample times. The combination of this slope information with the microphone signal product information described previously yields a composite calculation for indicating a valid blood pressure signal detection. A valid blood pressure signal is indicated if the product of the two microphone signals yields a negative value and either the slopes of the two signals have inverse signs or the slopes are both less than a selected slope threshold, e.g., 20°. It is apparent that if two signals are out of phase, one signal will be increasing (moving in a positive direction) while the other signal is decreasing (moving in a negative direction). Thus, the slopes of the two signals will be expected to have inverse signs. Near the signal peaks, where the slopes of the signals will be below the selected slope threshold, the signals will be at their highest amplitude and will be less likely to be affected by the presence of noise. The foregoing composite calculation also provides for the case where the distance D between the two microphones 16 and 18 is such that the blood pressure signal picked up by the two microphones is not exactly 180° out of phase. In such a case, the two out of phase signal peaks will not exactly coincide. Near the peaks, where the slopes of the signals will be less than the slope threshold, the slopes of the two signals may have the same sign even though the signals are substantially 180° out of phase. The composite calculation described would indicate a valid blood pressure signal detection for such a case, if the microphone signal product were negative, thereby allowing accurate detection of blood pressure sounds to be made even if the two microphones 16 and 18 are not placed exactly 180° out of phase with respect to the blood pressure sound signal.

If sampled signals are indicated to be valid blood pressure signals for more than a selected number of consecutive sample times, or a selected period of time, e.g., 2.5 milliseconds, the detection of a blood pressure sound is indicated. After a blood pressure sound detection is indicated, subsequent samples of the microphone signals are ignored for a selected pause period, e.g., 100 milliseconds. This prevents multiple blood pressure sound detections from being generated by the same event, i.e., following the same heart beat.

Figure 5:
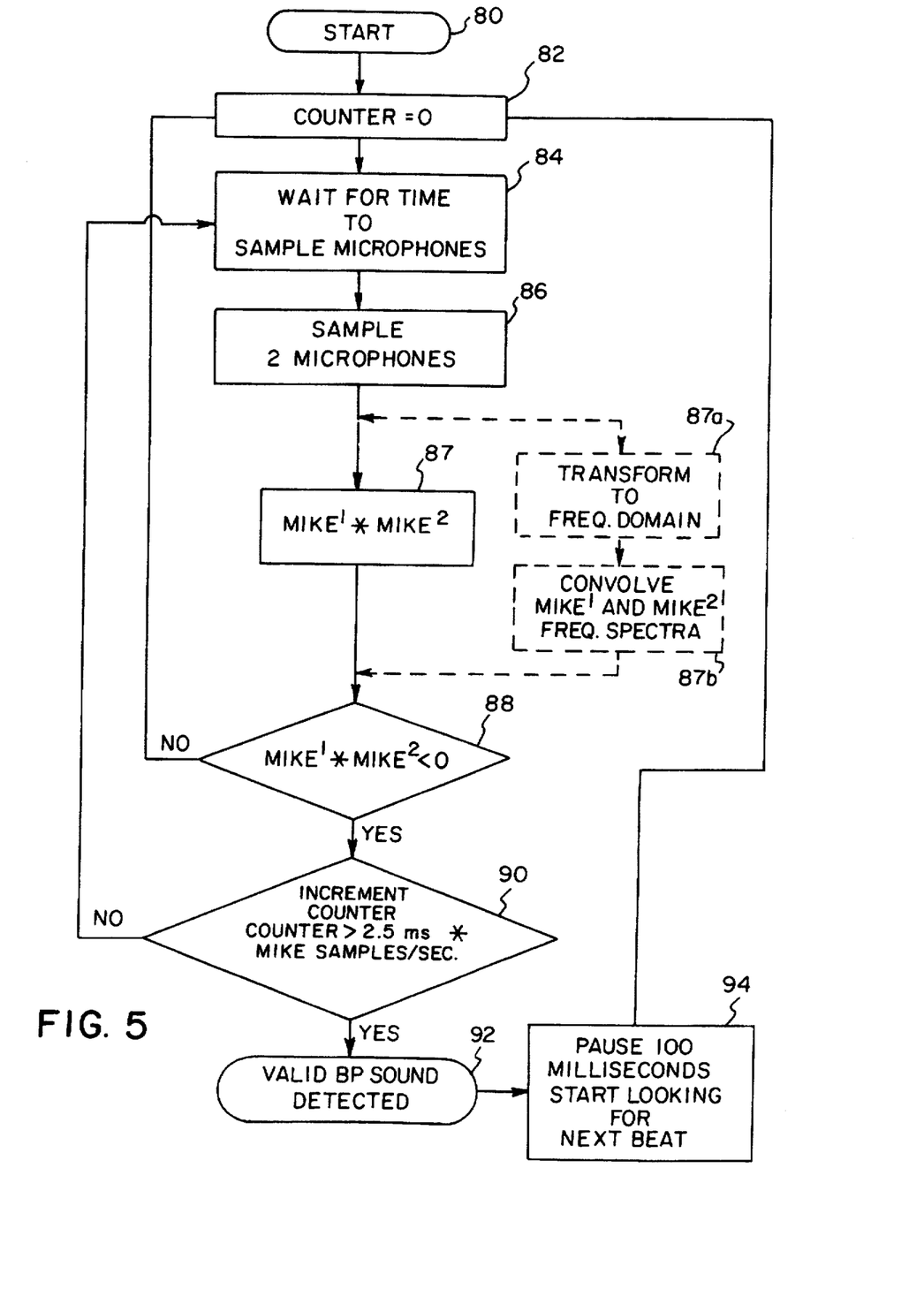
FIG. 5 is a flow chart diagram illustrating the steps of a method in accordance with the present invention for detect blood pressure sounds.

A description of the preferred calculation algorithm for detecting a blood pressure sound in the presence of significant noise is presented in graphical form in the flow chart of FIG. 5. Following the calculation start 80, a counter is set equal to zero at step 82. The counter will keep track of the number of consecutive indications of valid blood pressure signal detections. At step 84, the algorithm waits for the next sample time to be reached. At step 86, signals from the two microphones 16 and 18 are sampled.

At step 87, the two microphone signals are multiplied together. This may be accomplished in a conventional manner by multiplying the two sampled microphone signal values together in the microprocessor 22. Alternatively, as indicated by the steps 87a and 87b outlined in dashed lines, the multiplication may be accomplished through convolution of the two microphone signals in the frequency domain. It is well known that the multiplication of two functions in the time domain is equivalent to convolution of their spectra in the frequency domain. Thus, the two microphone signals may be converted to the frequency domain at step 87a, for example by use of a fast or sliding Fourier transform implemented in the microprocessor 22, and then the frequency spectra of the microphone signals convolved at step 87b to form the microphone signal product. After having determined the microphone signal product, by any method, the algorithm proceeds to step 88.

At step 88, the product of the two sampled microphone values are evaluated. If the product of the two microphone values is greater than or equal to zero, the two signals are not out of phase, and the sampled signals do not indicate valid blood pressure sounds. Thus, the algorithm returns to step 82 and the counter is reset to zero. If the product of the two microphone values is a negative value, a valid blood pressure signal is indicated. Thus, at step 90, the counter is incremented. If the counter indicates the detection of a selected number of consecutively valid blood pressure signals, e.g., the counter value is greater than 2.5 milliseconds multiplied by the microphone sampling rate per second, the detection of a blood pressure sound is indicated at step 92. At step 94 the algorithm pauses for a period of time, e.g., 100 milliseconds, before the algorithm continues at step 82 with the resetting of the counter. The algorithm then begins again to start looking for a valid blood pressure sound detection following the next heart beat. If, in step 92, the incremented counter indicates that less than the selected number of consecutive valid blood pressure signals has been detected, the algorithm returns to step 84 to await the next sample time, following which the algorithm calculations are repeated to determine whether the signal received at the next sample time is a valid blood pressure signal detection.

Figure 6:
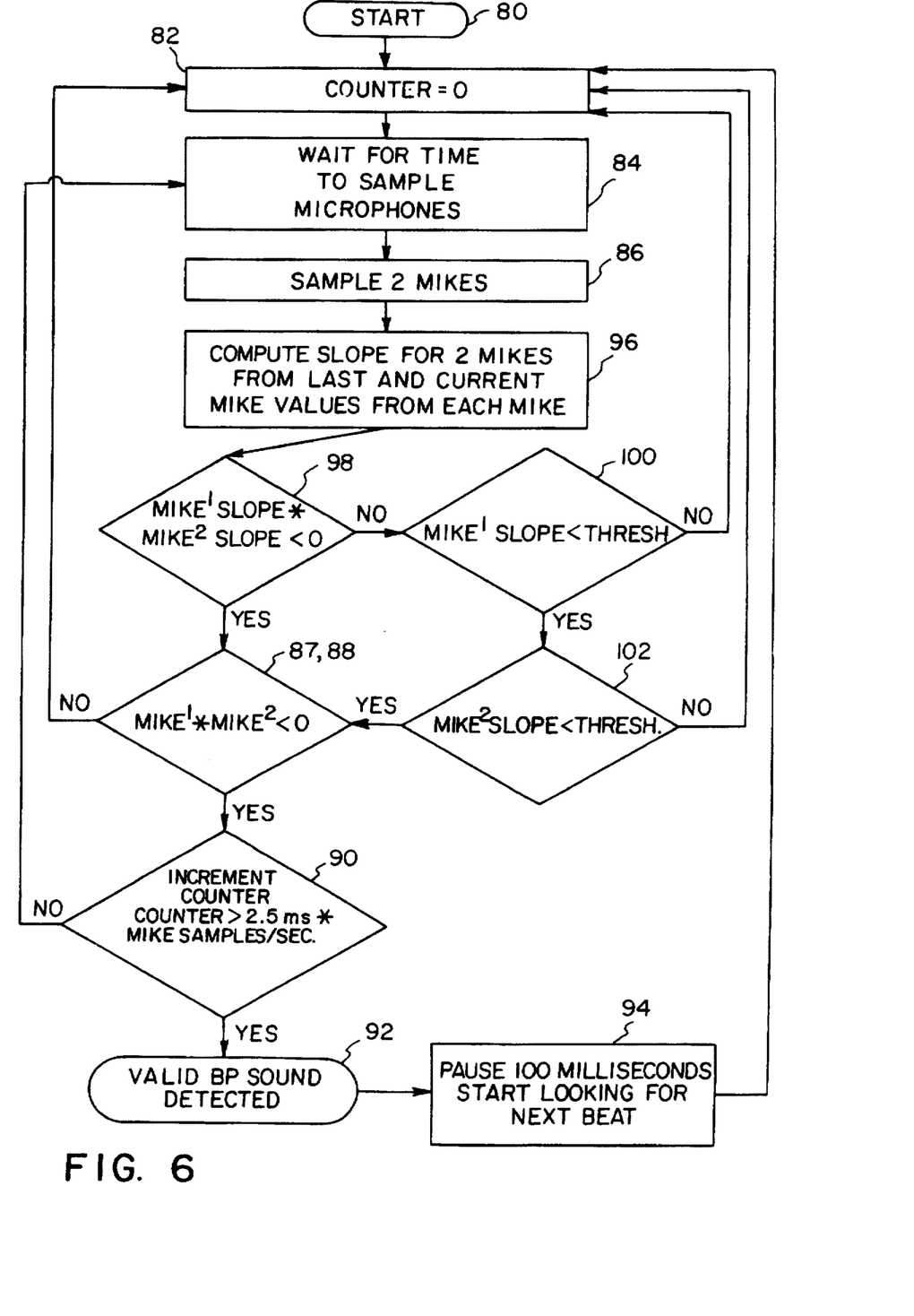
FIG. 6 is a flow chart diagram illustrating the steps of an alternative method in accordance with the present invention for detecting blood pressure sounds.

A description of an alternative composite calculation in accordance with the present invention for detecting a blood pressure sound in the presence of significant noise is presented in graphical form in the flow chart of FIG. 6. In FIG. 6, steps 80–94 are the same as in FIG. 5, and are thus labeled with the same reference numerals. In the composite calculation illustrated in FIG. 6, following step 86, where the two microphone signals are sampled, the algorithm proceeds to step 96. At step 96, the slope is determined for each of the two microphone signals using, for example, the difference between the current sampled microphone value and the last previous sampled microphone value from each microphone, as described previously. At step 98, the two microphone slopes are multiplied together. If the slopes of the two signals have inverse signs, the resulting product will be less than zero. This indicates that the signal may be a valid blood pressure signal, as two signals having slopes with inverse signs may be out of phase with each other, and so the algorithm proceeds to steps 87,88. If, however, the product of the two microphone signal slopes is equal to or greater than zero, the algorithm proceeds to step 100. At step 100, a determination is made whether the slope of the first microphone signal is less than the slope threshold, e.g., 20°. If not, the microphone signals do not indicate a valid blood pressure signal, and the algorithm returns to step 82 where the counter is reset to zero. If the slope of the first microphone signal is less than the threshold, the slope of the second microphone signal is compared to the slope threshold at step 102. If the slope of the second microphone signal is greater than the slope threshold, the microphone signals do not indicate a valid blood pressure signal, and the algorithm returns to step 82 where the counter is reset to zero. If the slope of the second microphone signal, as well as the slope of the first microphone signal, is found to be below the slope threshold, the algorithm proceeds to steps 87.88. From steps 87.88, the alternative composite calculation algorithm of FIG. 6 proceeds in the same manner as in the algorithm of FIG. 5 to indicate the detection of a valid blood pressure sound.

It is apparent that the algorithms illustrated in FIGS. 5 and 6 may be implemented in software to be run on the microprocessor 22 by a programmer of ordinary skill. It is also apparent that the order of operations of the steps illustrated in FIGS. 5 and 6 may be changed without altering the effectiveness of the algorithm. For example, it is apparent that the multiplication of the two microphone signal values indicated in step 87 (or steps 87a and 87b) may be accomplished before the slope of the two microphone signal values is calculated in step 96.

Other variations on the basic algorithms described may also be used. For example, in the preferred algorithm, the indication of a valid blood pressure signal increments a counter. In another embodiment in accordance with the present invention, the indication of a valid blood pressure signal may be stored in memory 28. The detection of a blood pressure sound may then be indicated when the number of valid blood pressure signal detections in a selected period exceeds a selected percentage. For example, a blood pressure sound detection may be indicated when more than 90% of the signals detected in a 2.5 ms period are valid blood pressure signal detections. Thus, the term "consecutive" valid blood pressure signal detections should be understood to include substantially consecutive detections as well.

Systolic and diastolic blood pressure levels of a patient may be determined based on the blood pressure sounds that are detected in accordance with the method of the present invention previously described. This may be accomplished in a usual manner employed for automatic auscultatory blood pressure determinations. An exemplary automated procedure for determining the systolic and diastolic blood pressure levels of a patient using the blood pressure monitoring system 10 shown in FIG. 1 employing the method for detecting blood pressure sounds of the present invention is as follows.

The inflatable cuff 12 is placed around the arm 14 of a patient with the two microphones 16 and 18 fixed therein placed against the arm 14 of the patient near the downstream end of the cuff and along the axis of a brachial artery. The centers of the microphones 16 and 18 are separated by the distance D, e.g., 2.5 centimeters, such that a blood pressure sound picked up by the two microphones 16 and 18 will be approximately 180° out of phase. A user may initiate the blood pressure monitoring cycle through, for example, the user input 26 to the microprocessor 22. Microprocessor 22 then provides control signals on the line 23 to the pressure controller 20 which will increase the pressure in the cuff 12 well above the maximum probable systolic blood pressure level to close the brachial artery in the arm 14. The microprocessor 22 then controls the pressure controller 20 to slowly reduce the pressure in the cuff 12. The pressure may be reduced at a slow continuous rate or in incremental steps. As the pressure is being slowly released from the cuff 12, the algorithm for extracting phase shift information from the two microphone signals is initiated. When the detection of a blood pressure sound is first indicated by the algorithm, the cuff pressure at that time, determined using the pressure transducer 30, is recorded by the microprocessor 22 in memory 28. This pressure corresponds to the systolic blood pressure level of the patient which may be displayed to the user on the system display 24. As the pressure in the cuff 12 continues to be gradually released, blood pressure sounds will continue to be detected by the algorithm. Each time a blood pressure sound detection is indicated, the cuff pressure at that time is recorded in memory 28 by the microprocessor 22. If, following a blood pressure sound detection, no further blood pressure sound detections are indicated for a selected period of time, the cuff pressure at the time of the last indication of a blood pressure sound detection is recorded in memory 28 as corresponding to the diastolic blood pressure level of the patient. The diastolic blood pressure level may then be displayed to the user on the blood pressure monitor system display 24. The remaining pressure in the cuff 12 may then be rapidly released.

Various other blood pressure monitoring systems and methods may employ the method and apparatus of the present invention for detecting blood pressure sounds in the presence of significant noise. For example, blood pressure sound detections may be made as the pressure in the cuff is slowly increased from below the minimum probable diastolic blood pressure level to above the systolic blood pressure level. In this case, the cuff pressure at the first detection of blood pressure sounds corresponds to the diastolic blood pressure level, and the cuff pressure at which blood pressure sounds are last detected corresponds to the systolic blood pressure level. The blood pressure measurement cycle may be terminated, and the pressure in the cuff 12 released, when blood pressure sounds are no longer detected. This method may be used to reduce the maximum pressure applied to the arm 14, since it is not necessary to estimate a high starting cuff pressure, well above the probable systolic blood pressure level, at which to initiate the blood pressure measurement cycle. Since the present invention is capable of distinguishing valid blood pressure sounds from noise, noise produced by the pump P will not prevent accurate blood pressure level determination during cuff inflation.

The present invention may also be used as a stage in a blood pressure monitoring system or method in which a patient's blood pressure is determined from a plot of the delay times between an ECG signal and the detection of a blood pressure sound at the inflatable cuff 12 for various cuff pressure levels. In such a blood pressure monitoring system the present invention would be used to accurately detect the occurrence of the blood pressure sound in the presence of significant noise. The blood pressure sound detection method and apparatus of the present invention may be employed by any blood pressure monitoring system or other medical device requiring the accurate detection of blood pressure sounds to improve the performance of such a device in highly noisy environments.

Although the present invention has been illustrated and described as implemented using a digital microprocessor 22, it is apparent that the present invention may be implemented using a combination of analog and/or digital components.

For example, the multiplication of the two filtered microphone signals may be accomplished using an analog multiplier. Conversion of the microphone signals to the frequency domain, and convolution of the resulting frequency domain spectra, may be accomplished using software or dedicated integrated circuits. The slopes of the two filtered microphone signals may be determined using an analog device. Signal comparisons may be accomplished using analog comparitors.

The detection of blood pressure sounds in accordance with the present invention has several advantages over previously known methods and devices for detecting blood pressure sounds. The present invention enables the accurate measurement of blood pressure under highly noisy conditions, such as during patient movement, shivering, and exercise, and in the presence of significant ambient vibration and noise. The present invention enables the accurate measurement of blood pressure during low flow states, such as cardiogenic shock, when the amplitude of blood pressure sounds is very low and can become dominated by even moderate noise levels. In such low flow states, the opening snap of the artery is detectable, even though Korotkoff sounds produced by blood flow turbulence are too low to be detected. Since the present invention relies on phase shift information and not amplitude information to detect blood pressure sounds, it can be applied to a wide variety of patient types without the necessity for calculating signal and noise thresholds and for making signal and noise amplitude threshold adjustments for each patient.

It is understood that this invention is not confined to the particular embodiments, implementations, and applications herein illustrated and described, but embraces all such modified forms thereof as come within the scope of the following claims.

What is claimed is:

1. A method for detecting a blood pressure sound in a patient, comprising the steps of:
   (a) placing a first microphone on the patient near the location of an artery, the first microphone producing a first microphone signal in response to blood pressure sounds and noise picked up by the first microphone;
   (b) placing a second microphone on the patient having a center separated a distance from a center of the first microphone such that a blood pressure sound picked up by the first microphone will be picked up out of phase by the second microphone, the second microphone producing a second microphone signal in response to blood pressure sounds and noise picked up by the second microphone;
   (c) applying pressure to the artery such that the artery will be forced closed during part of a heart beat cycle and will be forced open during part of the heart beat cycle when the patient's blood pressure exceeds the pressure applied to the artery, the opening of the artery causing a blood pressure sound to be produced;
   (d) selecting portions of the first and second microphone signals having characteristics corresponding to blood pressure sounds;
   (e) multiplying the selected portions of the first and second microphone signals at selected points in time to generate a microphone signal product; and
   (f) indicating the detection of a blood pressure sound when the microphone signal product is negative for multiple consecutive selected points in time corresponding to a selected time period.

2. The method of claim 1 wherein the step of indicating the detection of a blood pressure sound indicates the detection of a blood pressure sound when the microphone signal product is negative for multiple consecutive selected points in time corresponding to a selected time period of approximately 2.5 milliseconds.

3. The method of claim 1 comprising additionally the steps of preventing further indications of the detection of a blood pressure sound for a selected pause period after the indication of the detection of a blood pressure sound, and repeating the steps of selecting portions of the microphone signals, multiplying the microphone signals, and indicating the detection of a blood pressure sound after the selected pause period has ended.

4. The method of claim 3 wherein the selected pause period is approximately 100 milliseconds.

5. The method of claim 1 wherein the center of the second microphone is placed on the patient separated a distance from the center of the first microphone such that the blood pressure sound picked up by the first microphone will be picked up approximately 180 degrees out of phase by the second microphone.

6. The method of claim 5 wherein the center of the second microphone is placed on the patient separated by a distance of approximately 2.5 centimeters from the center of the first microphone.

7. The method of claim 1 wherein the step of applying pressure to the artery includes the step of inflating an inflatable cuff wrapped around an arm of the patient and wherein the first and second microphones are placed on the arm of the patient under the inflatable cuff near a down stream end of the cuff and along an axis of the artery.

8. The method of claim 7 wherein the first and second microphones are fixed in the inflatable cuff.

9. The method of claim 1 wherein the step of selecting portions of the first and second microphone signals includes the step of filtering the first and second microphone signals with filters having pass bands corresponding approximately to the frequency range of the blood pressure sound.

10. The method of claim 9 wherein the step of filtering the first and second microphone signals includes the step of filtering the first and second microphone signals with band pass filters having pass bands of approximately 30 Hz to 80 Hz.

11. The method of claim 1 wherein the step of multiplying the selected portions of the microphone signals includes the step of sampling the microphone signals at selected sampling points in time and multiplying the sampled microphone signals to generate the microphone signal product.

12. The method of claim 11 wherein the step of sampling the microphone signals at selected sampling points in time is performed at a sampling rate of between approximately 500 samples per second and approximately 2000 samples per second.

13. The method of claim 1 wherein the step of multiplying the selected portions of the microphone signals includes the steps of converting the first and second microphone signals to the frequency domain and then convolving the frequency domain spectra of the first and second microphone signals.

14. The method of claim 1 wherein the step of indicating the detection of a blood pressure sound indicates a blood pressure sound when the microphone signal product is negative and the absolute value of the microphone signal product exceeds a minimal noise threshold for multiple consecutive selected points in time corresponding to the selected time period.

15. The method of claim 1 comprising additionally the steps of determining slopes of the selected portions of the first and second microphone signals at the selected points in time and indicating the detection of a blood pressure sound when the microphone signal product is negative and either the slopes of the first and second microphone signals have inverse signs or the slopes of the first and second microphone signals are both less than a selected slope threshold at the selected point in time for multiple consecutive selected points in time corresponding to the selected time period.

16. A method for detecting blood pressure by blood pressure sounds in a patient, comprising the steps of:

(a) placing a first microphone on the patient near the location of an artery, the first microphone producing a first microphone signal in response to blood pressure sounds and noise picked up by the first microphone;

(b) placing a second microphone on the patient having a center separated a distance from a center of the first microphone such that a blood pressure sound picked up by the first microphone will be picked up out of phase by the second microphone, the second microphone producing a second microphone signal in response to blood pressure sounds and noise picked up by the second microphone;

(c) applying pressure to the artery at a plurality of pressure levels ranging from above a systolic blood pressure level of the patient to below a diastolic blood pressure level of the patient, the artery being forced open during part of the heart beat cycle when the patient's blood pressure exceeds the pressure applied to the artery, the opening of the artery causing a blood pressure sound to be produced;

(d) selecting portions of the first and second microphone siqnals having characteristics corresponding to blood pressure sounds;

(e) multiplying the selected portions of the first and second microphone siqnals at selected points in time to generate a microphone signal product;

(f) indicating the detection of a blood pressure sound when the microphone signal product is negative for multiple consecutive selected points in time corresponding to a selected time period;

(g) repeating the steps of selecting portions of the microphone signals, multiplying the microphone signals, and indicating the detection of a blood pressure sound at each of the plurality of pressure levels; and (h) displaying a systolic blood pressure level of the patient as a highest of the plurality of pressure levels at which a blood pressure sound is indicated as being detected and displaying a diastolic blood pressure level of the patient as a lowest of the plurality of pressure levels at which a blood pressure sound is indicated as being detected.

17. The method of claim 16 wherein the step of applying pressure to the artery at a plurality of pressure levels includes the step of slowly reducing pressure in an inflatable cuff from above a maximum probable systolic blood pressure level of the patient to a pressure level below the diastolic blood pressure level of the patient at which blood pressure sounds are no longer indicated as being detected to apply the plurality of pressure levels.

18. The method of claim 16 wherein the step of applying pressure to the artery at a plurality of pressure levels includes the step of slowly increasing pressure in an inflatable cuff from below the minimum probable diastolic blood pressure level of the patient to a pressure level above the systolic blood pressure level of the patient at which blood pressure sounds are no longer indicated as being detected to apply the plurality of pressure levels.

19. A method for detecting a blood pressure sound in a patient, comprising the steps of:

(a) placing a first microphone on the patient near the location of an artery, the first microphone producing a first microphone signal in response to blood pressure sounds and noise picked up by the first microphone;

(b) placing a second microphone on the patient having a center separated a distance from a center of the first microphone such that a blood pressure sound picked up by the first microphone will be picked up out of phase by the second microphone, the second microphone producing a second microphone signal in response to blood pressure sounds and noise picked up by the second microphone;

(c) applying pressure to the artery such that the artery will be forced closed during part of a heart beat cycle and will be forced open during part of the heart beat cycle when the patient's blood pressure exceeds the pressure applied to the artery, the opening of the artery causing a blood pressure sound to be produced;

(d) filtering the first and second microphone signals with band pass filters having pass bands corresponding approximately to the frequency range of the blood pressure sound;

(e) multiplying the filtered first and second microphone signals at selected points in time to generate a microphone signal product;

(f) indicating the detection of a valid blood pressure signal when the microphone signal product is negative; and (g) indicating the detection of a blood pressure sound when the detection of valid blood pressure signals are indicated for multiple consecutive selected points in time corresponding to a selected time period.

20. The method of claim 19 wherein the step of indicating the detection of a blood pressure sound indicates the detection of a blood pressure sound when valid blood pressure signals are detected for multiple consecutive selected points in time corresponding to a selected time period of approximately 2.5 milliseconds.

21. The method of claim 19 comprising additionally the steps of preventing further indications of the detection of a blood pressure sound for a selected pause period after the indication of the detection of a blood pressure sound, and repeating the steps of filtering the microphone signals, multiplying the microphone signals, indicating the detection of valid blood pressure signals, and indicating the detection of a blood pressure sound after the selected pause period has ended.

22. The method of claim 21 wherein the selected pause period is approximately 100 milliseconds.

23. The method of claim 19 wherein the center of the second microphone is placed on the patient separated a distance from the center of the first microphone such that the blood pressure sound picked up by the first microphone will be picked up approximately 180 degrees out of phase by the second microphone.

24. The method of claim 23 wherein the center of the second microphone is placed on the patient separated by a distance of approximately 2.5 centimeters from the center of the first microphone.

25. The method of claim 19 wherein the step of applying pressure to the artery includes the step of inflating an inflatable cuff wrapped around an arm of the patient and wherein the first and second microphones are placed on the arm of the patient under the inflatable cuff near a down stream end of the cuff and along an axis of the artery.

26. The method of claim 25 wherein the first and second microphones are fixed in the inflatable cuff.

27. The method of claim 19 wherein the step of filtering the first and second microphone signals includes the step of filtering the first and second microphone signals with band pass filters having a pass bands of approximately 30 Hz to 80 Hz.

28. The method of claim 19 wherein the step of multiplying the filtered microphone signals includes the step of sampling the microphone signals at selected sampling points in time and multiplying the sampled microphone signals to generate the microphone signal product.

29. The method of claim 28 wherein the step of sampling the microphone signals at selected sampling points in time is performed at a sampling rate of between approximately 500 samples per second and approximately 2000 samples per second.

30. The method of claim 19 wherein the step of multiplying the filtered microphone signals includes the steps of converting the first and second microphone signals to the frequency domain and then convolving the frequency domain spectra of the microphone signals.

31. A method for detecting blood pressure by blood pressure sounds in a patient, comprising the steps of:
- (a) placing a first microphone on the patient near the location of an artery, the first microphone producing a first microphone signal in response to blood pressure sounds and noise picked up by the first microphone;
- (b) placing a second microphone on the patient having a center separated a distance from a center of the first microphone such that a blood pressure sound picked up by the first microphone will be picked up out of phase by the second microphone, the second microphone producing a second microphone signal in response to blood pressure sounds and noise picked up by the second microphone;
- (c) applying pressure to the artery at a plurality of pressure levels ranging from above a systolic blood pressure level of the patient to below a diastolic blood pressure level of the patient, the artery being forced open during part of the heart beat cycle when the patient's blood pressure exceeds the pressure applied to the artery, the opening of the artery causing a blood pressure sound to be produced;
- (d) filtering the first and second microphone signals with band pass filters having pass bands corresponding approximately to the frequency range of the blood pressure sound;
- (e) multiplying the filtered first and second microphone signals at selected points in time to generate a microphone signal product;
- (f) indicating the detection of a valid blood pressure signal when the microphone signal product is negative;
- (g) indicating the detection of a blood pressure sound when the detection of valid blood pressure signals are indicated for multiple consecutive selected points in time corresponding to a selected time period;
- (h) repeating the steps of filtering the microphone signals, multiplying the microphone signals, indicating the detection of a valid blood pressure signal, and indicating the detection of a blood pressure sound at each of the plurality of pressure levels; and
- (i) displaying a systolic blood pressure level of the patient as a highest of the plurality of pressure levels at which a blood pressure sound is indicated as being detected and displaying a diastolic blood pressure level of the patient as a lowest of the plurality of pressure levels at which a blood pressure sound is indicated as being detected.

32. The method of claim 31 wherein the step of applying pressure to the artery at a plurality of pressure levels includes the step of slowly reducing pressure in an inflatable cuff from above a maximum probable systolic blood pressure level of the patient to a pressure level below the diastolic blood pressure level of the patient at which blood pressure sounds are no longer indicated as being detected to apply the plurality of pressure levels.

33. The method of claim 31 wherein the step of applying pressure to the artery at a plurality of pressure levels includes the step of slowly increasing pressure in an inflatable cuff from below the minimum probable diastolic blood pressure level of the patient to a pressure level above the systolic blood pressure level of the patient at which blood pressure sounds are no longer indicated as being detected to apply the plurality of pressure levels.

34. A method for detecting a valid blood pressure sound signal in a patient, comprising the steps of:
- (a) placing a first microphone on the patient near the location of an artery, the first microphone producing a first microphone signal in response to blood pressure sounds and noise picked up by the first microphone;
- (b) placing a second microphone on the patient having a center separated a distance from a center of the first microphone such that a blood pressure sound picked up by the first microphone will be picked up out of phase by the second microphone, the second microphone producing a second microphone signal in response to blood pressure sounds and noise picked up by the second microphone;
- (c) applying pressure to the artery such that the artery will be forced closed during part of a heart beat cycle and will be forced open during part of the heart beat cycle when the patient's blood pressure exceeds the pressure applied to the artery, the opening of the artery causing a blood pressure sound to be produced;
- (d) filtering the first and second microphone signals with a filter having a pass band corresponding approximately to the frequency range of the blood pressure sound;
- (e) multiplying the filtered first and second microphone signals at selected points in time to generate a microphone signal product;
- (f) determining slopes of the first and second filtered microphone signals at the selected points in time; and
- (g) indicating the detection of a blood pressure sound when the microphone signal product is negative and either the slopes of the first and second microphone signals have inverse signs or the slopes of the first and second microphone signals are both less than a selected slope threshold value for multiple selected points in time corresponding to a selected time period.

35. An apparatus for detecting blood pressure sounds in a patient, comprising:
- (a) an inflatable cuff adapted to be wrapped around a limb of a patient;
- (b) a first microphone fixed in the inflatable cuff, the first microphone producing a first microphone signal in response to blood pressure sounds and noise picked up by the first microphone;
- (c) a second microphone fixed in the inflatable cuff and having a center separated a distance from a center of the first microphone such that a blood pressure sound picked up by the first microphone will be picked up out of phase by the second microphone, the second microphone producing a second microphone signal in response to blood pressure sounds and noise picked up by the second microphone;

(d) means for inflating the inflatable cuff to thereby apply pressure to the limb of a patient such that an artery in the patient's limb will be forced closed during part of a heart beat cycle and will be forced open during part of the heart beat cycle when the patient's blood pressure exceeds the pressure applied to the artery, the opening of the artery causing a blood pressure sound to be produced;

(e) means for selecting portions of the first and second microphone signals having characteristics corresponding to blood pressure sounds;

(f) means for multiplying the selected portions of the first and second microphone signals at selected points in time to generate a microphone signal product;

(g) means for indicating the detection of a valid blood pressure signal when the microphone signal product is negative; and (h) means for indicating the detection of a blood pressure sound when the detection of valid blood pressure signals are indicated for multiple consecutive selected points in time corresponding to a selected time period.

36. The apparatus for detecting blood pressure sounds of claim 35 wherein the centers of the first and second microphones are separated by a distance such that the blood pressure sound picked up by the first microphone will be picked up approximately 180 degrees out of phase by the second microphone.

37. The apparatus for detecting blood pressure sounds of claim 36 wherein the centers of the first and second microphones are separated by a distance of approximately 2.5 centimeters.

38. The apparatus for detecting blood pressure sounds of claim 35 wherein the means for selecting portions of the first and second microphone signals includes band pass filters having pass bands corresponding approximately to the frequency range of the blood pressure sound.

39. The apparatus for detecting blood pressure sounds of claim 38 wherein the band pass filters have pass bands of approximately 30 Hz to 80 Hz.

40. The apparatus for detecting blood pressure sounds of claim 35 including means for sampling the filtered microphone signals at a sampling rate of between approximately 500 samples per second and approximately 2000 samples per second and means for multiplying the sampled microphone signals to generate the microphone signal product.

41. The apparatus for detecting blood pressure sounds of claim 35 wherein the means for multiplying the selected portions of the microphone signals includes means for converting the first and second microphone signals to the frequency domain and for convolving the frequency domain spectra of the first and second microphone signals.

42. The apparatus for detecting blood pressure sounds of claim 35 wherein the selected time period is approximately 2.5 milliseconds.

43. The apparatus for detecting blood pressure sounds of claim 35 comprising additionally means for determining slopes of the selected portions of the first and second microphone signals at the selected points in time and means for indicating the detection of a valid blood pressure signal when the microphone signal product is negative and either the slopes of the first and second microphone signals have inverse signs or the slopes of the first and second microphone signals are both less than a selected slope threshold.

44. An apparatus for detecting blood pressure by blood pressure sounds in a patient, comprising:

(a) an inflatable cuff adapted to be wrapped around a limb of a patient;

(b) a first microphone fixed in the inflatable cuff, the first microphone producing a first microphone signal in response to blood pressure sounds and noise picked up by the first microphone;

(c) a second microphone fixed in the inflatable cuff and having a center separated a distance from a center of the first microphone such that a blood pressure sound picked up by the first microphone will be picked up out of phase by the second microphone, the second microphone producing a second microphone signal in response to blood pressure sounds and noise picked up by the second microphone;

(d) means for inflating and deflating the inflatable cuff to apply pressure to the limb of the patient at a plurality of pressure levels ranging from above a systolic blood pressure level of the patient to below a diastolic blood pressure level of the patient, an artery in the patient's limb being forced open during part of the heart beat cycle when the patient's blood pressure exceeds the pressure applied to the artery, the opening of the artery causing a blood pressure sound to be produced;

(e) means for selecting portions of the first and second microphone siqnals having characteristics corresponding to blood pressure sounds;

(f) means for multiplying the selected portions of the first and second microphone siqnals at selected points in time to generate a microphone signal product;

(g) means for indicating the detection of a valid blood pressure signal when the microphone signal product is negative;

(h) means for indicating the detection of a blood pressure sound when the detection of valid blood pressure signals are indicated for multiple consecutive selected points in time corresponding to a selected time period;

(i) means for measuring the cuff pressure at each of the plurality of pressure levels;

(j) means for selecting portions of the microphone signals, multiplying the microphone signals, indicating the detection of a valid blood pressure signal, and indicating the detection of a blood pressure sound at each of the plurality of pressure levels; and (k) means for displaying a systolic blood pressure level of the patient as a highest of the measured cuff pressure levels at which a blood pressure sound is indicated as being detected and displaying a diastolic blood pressure level of the patient as a lowest of the measured cuff pressure levels at which a blood pressure sound is indicated as being detected.

45. The apparatus for detecting blood pressure sounds of claim 44 wherein the means for measuring the cuff pressure includes a pressure transducer.

* * * * *